United States Patent
Lentz et al.

(10) Patent No.: US 6,981,382 B2
(45) Date of Patent: Jan. 3, 2006

(54) DISTAL END FOR CRYOABLATION CATHETERS

(75) Inventors: David J. Lentz, La Jolla, CA (US); Matt M. Riordan, Saratoga, CA (US); Eric Ryba, San Diego, CA (US)

(73) Assignee: CryoCor, Inc., San Diego, CA (US)

( * ) Notice: Subject to any disclaimer, the term of this patent is extended or adjusted under 35 U.S.C. 154(b) by 0 days.

(21) Appl. No.: 10/626,887

(22) Filed: Jul. 24, 2003

(65) Prior Publication Data

US 2005/0016188 A1    Jan. 27, 2005

(51) Int. Cl.
*F25D 15/00* (2006.01)
*A61B 18/02* (2006.01)

(52) U.S. Cl. ............................. 62/119; 606/22; 606/23; 606/25

(58) Field of Classification Search .................. 606/20, 606/21, 22, 23, 25, 26, 24; 62/293, 119
See application file for complete search history.

(56) References Cited

U.S. PATENT DOCUMENTS

| | | |
|---|---|---|
| 3,696,813 A | 10/1972 | Wallach |
| 3,913,581 A | 10/1975 | Ritson et al. |
| 3,951,152 A | 4/1976 | Crandell et al. |
| 4,018,227 A | 4/1977 | Wallach |
| 5,139,496 A | 8/1992 | Hed |
| 5,147,355 A | 9/1992 | Friedman et al. |
| 5,281,213 A | 1/1994 | Milder et al. |
| 5,281,215 A | 1/1994 | Milder |
| 5,423,807 A | 6/1995 | Milder |
| 5,452,582 A | 9/1995 | Longsworth |
| 5,502,972 A * | 4/1996 | Howard et al. ............... 62/623 |
| 5,520,682 A * | 5/1996 | Baust et al. .................. 606/24 |
| 5,759,182 A | 6/1998 | Varney et al. |
| 5,876,399 A | 3/1999 | Chia et al. |
| 5,899,898 A | 5/1999 | Arless et al. |
| 5,899,899 A | 5/1999 | Arless et al. |
| 5,957,963 A * | 9/1999 | Dobak, III .................. 607/104 |
| 5,992,158 A | 11/1999 | Goddard et al. |
| 6,024,740 A | 2/2000 | Lesh et al. |
| 6,048,919 A | 4/2000 | McCullough |
| 6,117,101 A | 9/2000 | Diederich et al. |
| 6,139,544 A | 10/2000 | Mikus et al. |
| 6,235,019 B1 | 5/2001 | Lehmann et al. |
| 6,237,355 B1 | 5/2001 | Li |
| 6,245,064 B1 | 6/2001 | Lesh et al. |

(Continued)

FOREIGN PATENT DOCUMENTS

DE    101 18 805 A1    11/2002

(Continued)

*Primary Examiner*—Cheryl Tyler
*Assistant Examiner*—Richard L. Leung
(74) *Attorney, Agent, or Firm*—Nydegger & Associates

(57) ABSTRACT

A system and method for transferring heat requires a supply tube connected in fluid communication with a capillary tube. A tip member is positioned to surround the distal end of the capillary tube to create a cryo-chamber. In operation, a liquid refrigerant is introduced into the supply tube at a working pressure (e.g. 450 psia). The pressure is then significantly reduced on the liquid refrigerant as it transits through the capillary tube. The refrigerant then exits the distal end of the capillary tube, still in its liquid state. Inside the cryo-chamber, at a pressure of less than about one atmosphere, the refrigerant transitions into its gaseous state. The resultant refrigeration causes heat to transfer into the cryo-chamber.

16 Claims, 2 Drawing Sheets

U.S. PATENT DOCUMENTS

| | | |
|---|---|---|
| 6,251,105 B1 | 6/2001 | Mikus et al. |
| 6,280,439 B1 | 8/2001 | Martin et al. |
| 6,283,959 B1 | 9/2001 | Lalonde et al. |
| 6,383,180 B1 | 5/2002 | Lalonde et al. |
| 6,407,149 B1 | 6/2002 | McCullough |
| 6,468,268 B1 | 10/2002 | Abboud et al. |
| 6,471,693 B1 | 10/2002 | Carroll et al. |
| 6,527,769 B2 | 3/2003 | Langberg et al. |
| 6,540,740 B2 | 4/2003 | Lehmann et al. |
| 6,562,030 B1 | 5/2003 | Abboud et al. |
| 6,569,158 B1 | 5/2003 | Abboud et al. |
| 6,575,966 B2 | 6/2003 | Lane et al. |
| 6,579,287 B2 | 6/2003 | Wittenberger et al. |
| 6,585,728 B2 | 7/2003 | Heiner et al. |
| 6,585,729 B1 | 7/2003 | Eum |
| 6,589,234 B2 * | 7/2003 | Lalonde et al. ............... 606/23 |
| 6,592,577 B2 | 7/2003 | Abboud et al. |
| 6,595,988 B2 | 7/2003 | Wittenberger et al. |
| 6,602,247 B2 | 8/2003 | Lalonde |
| 6,605,087 B2 | 8/2003 | Swartz et al. |
| 6,629,972 B2 | 10/2003 | Lehmann et al. |
| 6,635,053 B1 | 10/2003 | Lalonde et al. |
| 6,733,494 B2 | 5/2004 | Abboud et al. |
| 6,755,823 B2 | 6/2004 | Lalonde |
| 6,761,714 B2 | 7/2004 | Abboud et al. |
| 2001/0021847 A1 | 9/2001 | Abboud et al. |
| 2001/0025075 A1 | 9/2001 | Smith et al. |
| 2002/0025998 A1 | 2/2002 | McCollough et al. |
| 2002/0062122 A1 | 5/2002 | Lehmann et al. |
| 2002/0111612 A1 | 8/2002 | Lalonde et al. |
| 2002/0115989 A1 | 8/2002 | Abboud et al. |
| 2002/0120258 A1 * | 8/2002 | Lalonde ...................... 606/23 |
| 2002/0198578 A1 | 12/2002 | Dobak, III |
| 2003/0004504 A1 | 1/2003 | Abboud et al. |
| 2003/0009160 A1 | 1/2003 | Carroll et al. |
| 2003/0018326 A1 | 1/2003 | Abboud et al. |
| 2003/0040740 A1 | 2/2003 | Kovalcheck et al. |
| 2003/0097124 A1 | 5/2003 | Lehmann et al. |
| 2004/0049178 A1 | 3/2004 | Abboud et al. |
| 2004/0054361 A1 | 3/2004 | Lehmann et al. |

FOREIGN PATENT DOCUMENTS

EP     1 398 002 A1     3/2004

* cited by examiner

DISTAL END FOR CRYOABLATION CATHETERS

FIELD OF THE INVENTION

The present invention pertains generally to interventional medical devices that can be advanced into the vasculature of a patient. More particularly, the present invention pertains to cryo-catheters that are useful for cryoablating tissue in the vasculature. The present invention is particularly, but not exclusively, useful for the construction and deployment of a cryo-catheter wherein a refrigerant fluid transitions from a liquid to a gaseous state, at an operational site in the vasculature, to establish cryoablation temperatures that are below approximately minus eighty four degrees Centigrade.

BACKGROUND OF THE INVENTION

Medical devices that can be advanced into the vasculature of a patient, and properly positioned at a site for an in-situ procedure, have several structural requirements in common with each other. Most importantly, they must be properly dimensioned to allow them to be advanced into the vasculature. This requires they be long and slender. Also, they must be steerable, bio-compatible, flexible and have sufficient structural strength to maintain their integrity while they are employed in the vasculature. With all of this in mind, the interventional device must also be fully capable of performing its intended function.

Recently, there has been substantial interest in medical procedures involving the cryo-ablation of tissue. In general, such procedures are intended to freeze specifically identified tissue. One procedure for which the cryoablation of tissue is known to be particularly efficacious is in the treatment of atrial fibrillation in the left atria of the heart. It happens, however, that cryoablation in general, and this procedure in particular, preferably requires temperatures below about minus eighty four degrees Centigrade (−84° C.). In order to generate such temperatures deep in the vasculature of a patient, several heat transfer principles need to be considered. Specifically, not only must such very low temperatures be generated, these temperatures must be somehow confined to the proximity where tissue is to be cryoablated.

Fourier's law of heat conduction states that the rate at which heat is transferred through a body, per unit cross sectional area, is proportional to the temperature gradient existing in the body (dQ/dt=rate of heat transfer). Mathematically, this phenomenon is expressed as:

$$dQ/dt = -\lambda A \, dT/dx$$

where $\lambda$ is the material's thermal conductivity, "A" is the cross sectional area through which heat is to be transferred, and dT/dx is the local temperature gradient. In the context of a cryo-catheter, "A" will be predetermined and will be necessarily limited by space considerations. Further, because high thermally conductive materials can be used in the manufacture of the cryo-catheter (e.g. copper), the thermal conductivity ($\lambda$) for a cryoablation procedure is effectively controlled by the relatively low conductivity of the tissue that is to be ablated. Thus, it can be appreciated that the local temperature gradient "dT/dx" is a control variable of significant importance. In particular, it is desirable that the local temperature gradient between tissue at an operational site, and the refrigerant in a cryo-catheter, be as great as possible. Stated differently, it is desirable to have cryo-catheter temperatures at the operational site that are as low as possible.

In addition to the temperature gradient effect discussed above, it is also to be appreciated that a substantial amount of heat transfer in a substance can result without any change in temperature. Specifically, this phenomenon involves latent heat and occurs wherever a substance, such as a fluid refrigerant, changes state. By definition, "latent heat" is the heat which is required to change the state of a unit mass of a substance from a solid to a liquid, or from a liquid to a gas, without a change of temperature. In the case of a fluid refrigerant, it can be said that prior to such a state change, the liquid refrigerant is "refrigerant in excess". On the other hand, after the fluid refrigerant begins to boil (i.e. change state from liquid to gas) the gas refrigerant is "refrigerant limited". Insofar as cryo-catheters are concerned, due to their requirement for low operational temperatures, it is desirable to obtain the additional refrigeration potential that results during the transfer of latent heat. Stated differently, it is preferable for the refrigerant to stay in its liquid state (i.e. remain "refrigerant in excess") until employed for cryoablation.

At this point it should also be noted that there is a significant benefit which is obtained by maintaining a fluid refrigerant in its liquid state while it transits through a system. Specifically, this benefit comes from the fact that, any water entrained in the liquid refrigerant is prevented from forming as frost or ice that could clog the system, so long as the refrigerant remains liquid. This is a particularly important consideration whenever a system requires that the refrigerant pass through small or narrow orifices.

As discussed above, for the operation of a cryoablation system, it is necessary to select a fluid refrigerant that is capable of generating very low temperatures (i.e. <−84° C.). Prior to its use in the system, however, the fluid refrigerant is typically stored in vessels under very high pressure (i.e. around 700 psia). On the other hand, when it is to be used in a cryo-catheter, the pressure on the refrigerant needs to be reduced in stages to about one atmosphere. In addition to the refrigeration effect, an important consideration here is that the pressure be reduced to a level below normal blood pressure for safety reasons.

Although there are several well known ways in the pertinent art for reducing the pressure on a fluid, a convenient way for accomplishing this pressure reduction in a cryo-catheter is by passing the fluid refrigerant through a capillary tube. For capillary tubes that can be considered as being long, straight, uniform pipes, the "Darcy equation" is applicable. According to the Darcy equation a pressure drop along the length of the pipe (tube) (i.e. head loss "$h_f$") can be mathematically expressed as:

$$h_f = f(l/d)(V^2/2g)$$

In the above expression: "f" is a friction factor, "l" is the length of the tube, "d" is the diameter of the tube, "V" is the velocity of the fluid through the tube, and "g" is the acceleration due to gravity.

From the Darcy equation it is to be noted that the head loss ($h_f$) is proportional to the ratio "l/d". This is the same as saying that the head loss is inversely proportional to the aspect ratio ("d/l") of the pipe (tube). Regardless how viewed, the pressure drop along the entire length of a pipe will increase by reducing the inside diameter of the pipe "d" or by increasing the length "l" of the pipe. In any event, the dimensions of a tube that is to be used in a cryo-catheter for the purpose of reducing pressure on a fluid refrigerant should be selected so that the fluid is "refrigerant in excess"

(i.e. in a liquid state) as it transits through the tube. Empirical results can be helpful when determining the most effective dimensions for such a tube.

In light of the above, it is an object of the present invention to provide a heat transfer system that will maintain a fluid refrigerant in a liquid state during a pressure drop on the fluid that is greater than four hundred psia, when the final pressure on the fluid is to be less than approximately one atmosphere. Another object of the present invention is to provide a heat transfer system that effectively avoids frost or ice build-up in the system as refrigerant passes through a relatively small orifice. Still another object of the present invention is to provide a heat transfer system that can be safely introduced into the vasculature of a patient where it will create temperatures as low as about minus eighty four degrees Centigrade. Another object of the present invention is to provide a heat transfer system that is relatively easy to manufacture, is simple to use and is comparatively cost effective.

SUMMARY OF THE INVENTION

A cryo-catheter (i.e. heat transfer system) in accordance with the present invention includes a hollow supply tube having a distal end that is connected in fluid communication with the proximal end of a capillary tube. Additionally, a tip member is positioned to surround the distal end of the capillary tube to thereby create a cryo-chamber that is located at the distal end of the cryo-catheter.

The source of refrigerant fluid mentioned above is connected in fluid communication with the proximal end of the supply tube. Preferably, the refrigerant fluid is nitrous oxide ($N_2O$), and it is introduced into the supply tube at a working pressure "$p_w$" that will typically be in a range between four hundred and four hundred and fifty psia (400–450 psia). The refrigerant fluid then sequentially transits through the supply tube and through the capillary tube. Importantly, as the refrigerant fluid exits from the distal end of the capillary tube, it is substantially still in a liquid state. The dimensions of both the supply tube and capillary tube, as well as the working pressure "$p_w$" for the refrigerant fluid are specifically chosen for this purpose.

For the construction of the present invention, the supply tube is formed with a lumen having a length "$l_s$" and a diameter "$d_s$". Further, the capillary tube is formed with a lumen having a length "l" and a diameter "d". More specifically, the diameter "d" of the capillary tube lumen is less than the diameter "$d_s$" of the supply tube lumen. As specifically intended for the present invention, the refrigerant fluid experiences much more resistance and a much greater pressure drop as it passes through the capillary tube than it did while passing through the supply tube. In detail, while the supply tube may have an aspect ratio "$d_s/l_s$" of around 0.1 or 0.05, the capillary tube will preferably have an aspect ratio "d/l" that is in a range of 0.0008 to 0.0017. When calculating the aspect ratio for the capillary tube, the length "l" will preferably be in a range between approximately four and one half inches and ten inches (4.5 in–10 in.), and the diameter "d" of the capillary tube will be between about 0.008 inches and 0.010 inches.

As indicated above, for the operation of the present invention, the working pressure "$p_w$" on the refrigerant fluid at the proximal end of the supply tube, will preferably be in a range between four hundred and four hundred and fifty psia (400–450 psia). On the other hand, the tip pressure "$p_t$" on the refrigerant fluid as it leaves the distal end of the capillary tube and enters the cryo-chamber is preferably less than about one atmosphere. Within this environment, after the refrigerant fluid has transitioned into its gaseous state in the cryo-chamber, it will create a tip temperature "$T_t$" that is less than about minus eighty four degrees Centigrade ($T_t$<−84° C.).

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
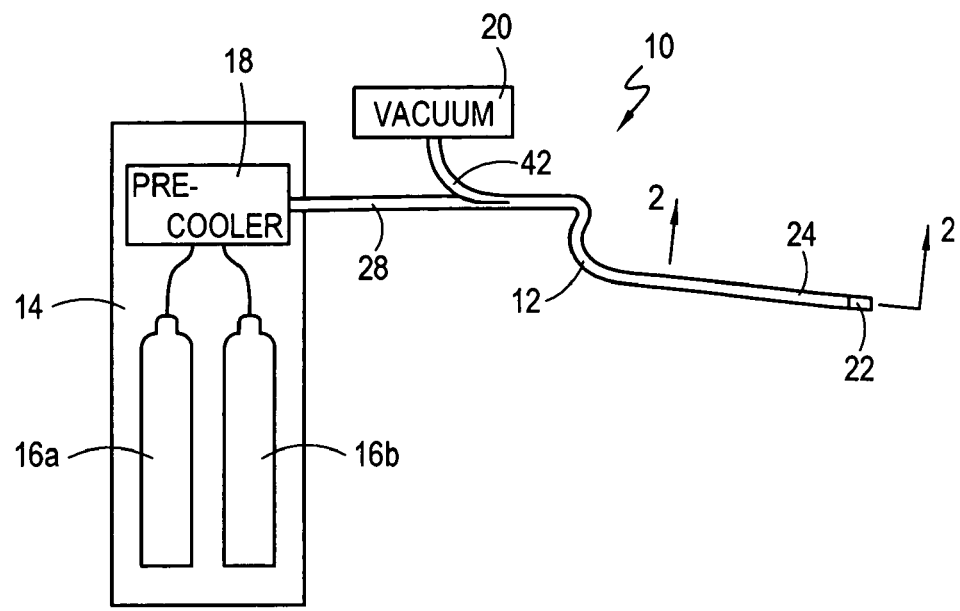
FIG. 1 is a schematic view of a system incorporating the present invention.

Referring initially to FIG. 1, a system in accordance with the present invention is shown and is generally designated 10. In detail, the system 10 is shown to include a cryo-catheter 12 that is connected to a console 14 and in fluid communication with a pair of fluid refrigerant sources 16a and 16b that are mounted inside the console 14. The sources 16a and 16b shown in FIG. 1 are, however, only exemplary. As envisioned for the present invention, the refrigerant sources 16a and 16b may be of any type pressure vessel known in the pertinent art that is suitable for holding a fluid under relatively high pressures (e.g. 700 psia). For the purposes of the present invention, the fluid refrigerant that is held in sources 16a and 16b will preferably be nitrous oxide ($N_2O$). Still referring to FIG. 1 it is seen that the fluid refrigerant sources 16a and 16b are connected in fluid communication with a pre-cooler 18. The pre-cooler 18, in turn, is connected in fluid communication with the cryo-catheter 12. Further, for purposes to be subsequently disclosed, the cryo-catheter 12 is connected in fluid communication to a vacuum source 20.

At the extreme distal end of the cryo-catheter 12, is a tip 22. Importantly, the tip 22 should be made of a material having very high thermal conductivity, such as copper or steel which respectively have thermal conductivities of 385 and 46 Watts/° K*m. To put this in perspective, water has a thermal conductivity of only 0.627 Watts/° K*m.

Figure 2:
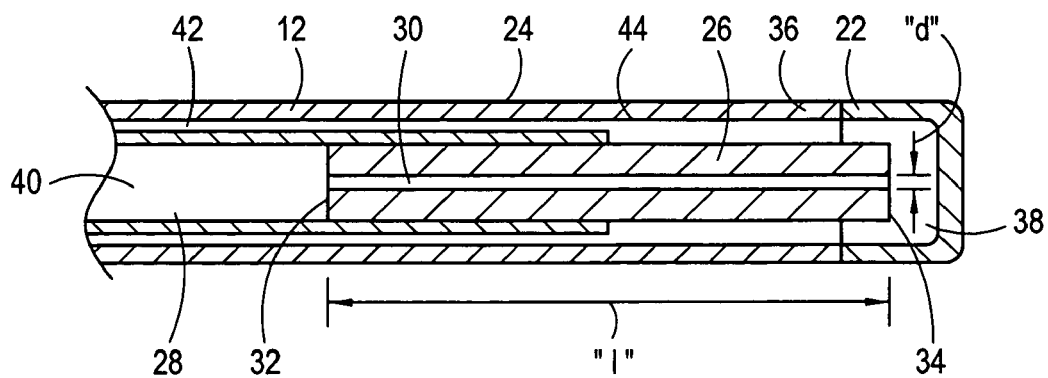
FIG. 2 is a cross-sectional view of the distal portion of a cryo-catheter as seen along the line 2—2 in FIG. 1.

Referring now to FIG. 2, it will be seen that inside the distal portion 24 of cryo-catheter 12, a capillary tube 26 is connected to a supply tube 28. Preferably, both the capillary tube 26 and the supply tube 28 will be made of a polymer material that has a relatively low thermal conductivity. Further, the capillary tube 26 preferably has a length "l" that is equal to, or preferably, shorter than the length "$l_s$" of supply tube 28 ($l \leq l_s$). While the supply tube 28 is dimensioned so as to cause a minimal pressure drop on the fluid refrigerant as it passes through the supply tube 28, this is not so insofar as the capillary tube 26 is concerned. More specifically, in its structural aspects, the capillary tube 26 is formed with a lumen 30 that extends the entire length of the capillary tube 26 from its proximal end 32 to its distal end 34. As indicated, the lumen 30 of capillary tube 26 has a diameter "d" and a length "l". In their relationship to each other, the diameter and length of lumen 30 in capillary tube 26 define an aspect ratio "d/l" that effectively determines the fluid flow characteristics of the capillary tube 26. For the present invention, the aspect ratio "d/l" is preferably in a range of 0.0008 to 0.0017, with the diameter "d" being selected in the range of about 0.008 inches to about 0.010 inches, and the length "l" being selected in the range of approximately four and one half inches to approximately ten inches. Recall, for selected embodiments, the supply tube 28 may also be of length "l". Preferably, however, the capillary tube 26 will be shorter than the supply tube 28.

Still referring to FIG. 2 it is to be appreciated that the tip 22 is attached to the distal end 36 of the cryo-catheter 12. Specifically, the tip 22 is attached to the cryo-catheter 12 to create a cryo-chamber 38 around the distal end 34 of the capillary tube 26. The structural consequence here is that a fluid refrigerant in the lumen 40 of the supply tube 28 can flow from lumen 40, through the lumen 30 of the capillary tube 26, and into the cryo-chamber 38. Once the fluid is in the cryo-chamber 38, it can then be exhausted from the cryo-catheter 12 through the return path 42 by vacuum source 20. As shown, this return path 42 is established between the wall 44 of the cryo-catheter 12 and the respective outside surfaces of the capillary tube 26 and the supply tube 28. The thermodynamics of fluid flow along this pathway through the cryo-catheter 12 will be best appreciated with reference to FIG. 3.

Figure 3:
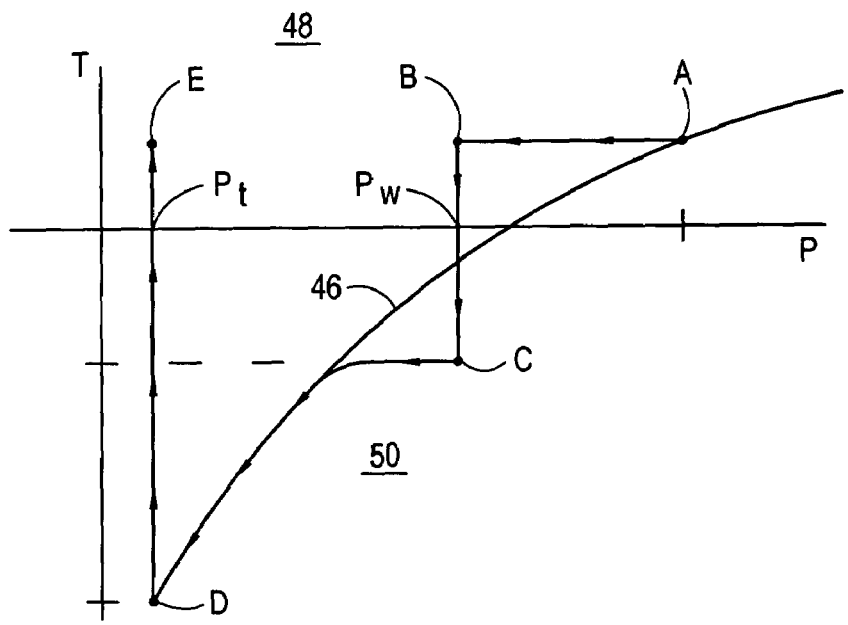
FIG. 3 is a graphical plot of pressure vs. temperature for a duty cycle in the operation of the present invention.

FIG. 3 shows a pressure-temperature graph for a fluid refrigerant, such as nitrous oxide ($N_2O$), and a typical plot of the relationship between these variables as the refrigerant transits through the system 10 of the present invention. In particular, the curve 46 shown in FIG. 3 is indicative of a phase change for the refrigerant between a gaseous state 48 and a liquid state 50.

When cross-referencing FIG. 3 with FIG. 1 it is to be appreciated that the pressure and temperature conditions for the fluid refrigerant, as stored in the fluid refrigerant sources 16a and 16b, is indicated by the point A in FIG. 3. Specifically, it is expected that the fluid refrigerant will be stored in sources 16a and 16b at ambient temperature (i.e. room temperature) under a pressure of about 700 psig. When in use, a pressure regulator (not shown) then reduces the pressure on the fluid refrigerant to a working pressure ("$p_w$") that will be about 400 to 450 psia (see point B in FIG. 3). The pre-cooler 18 then reduces the temperature of the fluid refrigerant to a temperature of about minus forty five degrees Centigrade while maintaining the fluid refrigerant at the working pressure "$p_w$" (see point C in FIG. 3). Note that with this cooling, the fluid refrigerant is transformed into its liquid state 50. Also, it is to be appreciated that the fluid refrigerant is introduced into the supply tube 28 under the conditions indicated at point C.

In overview, conditions on the fluid refrigerant change from the values at point C to those at point D on the graph shown in FIG. 3, as the fluid refrigerant transits through the supply tube 28 and the capillary tube 26. The vast majority of this change, however, occurs in the capillary tube 26. Specifically, as the fluid refrigerant enters the lumen 30 at the proximal end 32 of capillary tube 26, it will be at a temperature of about minus forty five degrees Centigrade. Also, it will be under a working pressure "$p_w$" of about four hundred to four hundred and fifty psia (point C). As the fluid refrigerant transits capillary tube 26, the pressure on the fluid refrigerant in lumen 30 is reduced from "$p_w$" in the supply tube 28 to a tip pressure "$p_t$" in the cryo-chamber 38. For the present invention, the tip pressure "$p_t$" will preferably be less than approximately one atmosphere of pressure. Accordingly, as intended for the present invention, there will be a pressure drop (i.e. head loss "$h_l$") that will be around 450 psia.

As shown in FIG. 3, along with the pressure reduction from "$p_w$" to "$p_t$" (i.e. head loss "$h_l$"), the temperature of the fluid refrigerant will be reduced to a tip temperature "$T_t$" at the distal end 34 of the capillary tube 26 (point D in FIG. 3). For the present invention, the tip temperature "$T_t$" in the cryo-chamber 38 will be less than about minus eighty four degrees Centigrade. Importantly, as this temperature is achieved, the fluid refrigerant transits the capillary tube 26 from its proximal end 32 (point C in FIG. 3) to its distal end 34 (point D in FIG. 3) in its liquid state 50.

As the fluid refrigerant exits into the cryo-chamber 38 from the distal end 34 of capillary tube 26 it evaporates. After boiling has occurred, the consequent rapid rise in temperature of the fluid refrigerant in the cryo-chamber 38 is due, in large part, to heat transfer from the tissue being cryoablated in the patient (not shown). In FIG. 3, this heat transfer is represented by the change in conditions on the fluid refrigerant (now in its gaseous state 48) indicated by the transition from the tip temperature "$T_t$" (point D) to a generally ambient temperature (point E). FIG. 3 also indicates that the heat transfer to the fluid refrigerant in the cryo-chamber 38 is accomplished at a substantially constant tip pressure "$p_t$". As mentioned above, the establishment and maintenance of this tip pressure "$p_t$" is facilitated by the action of the vacuum source 20 that operates to evacuate the fluid refrigerant from the system 10.

In the operation of the present invention, the vacuum source 20 is activated to establish a tip pressure "$p_t$" in the cryo-chamber 38 that is less than about one atmosphere. The exact value of this tip pressure "$p_t$" may, however, vary to some extent. Importantly, "$p_t$" is established to evacuate fluid refrigerant from the system 10 and reduce back pressure on the cryo-chamber 38.

Figure 4:
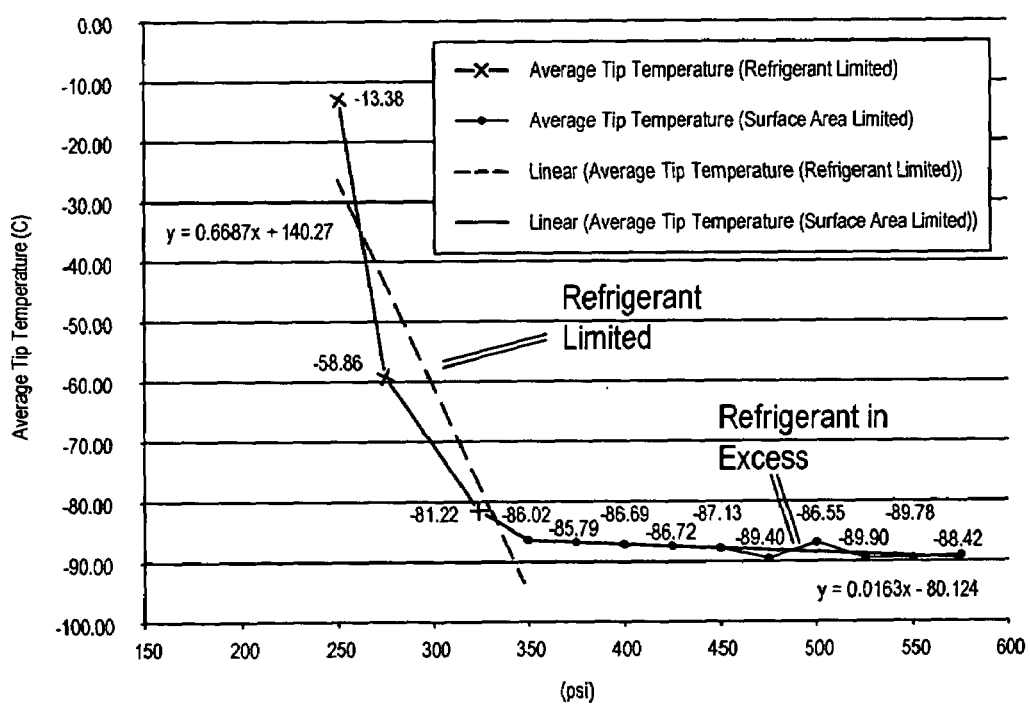
FIG. 4 is an exemplary graphical representation of changes in the tip temperature ($T_t$) of a cryo-catheter as a function of the working pressure ($p_w$) on the fluid refrigerant.

FIG. 4 is a plot of the variations in the tip temperature "$T_t$" at the distal end 34 of capillary tube 26, as a function of the working pressure ("$p_w$") at the proximal end 32 of the capillary tube 26. In particular, the specific measurements shown in FIG. 4 were obtained using a capillary tube 26 having a length "l" equal to 7.35 inches and a diameter "d" equal to 0.008 inches (aspect ratio "d/l"=0.00109). Although the plot shown in FIG. 4 is specific for a capillary tube 26 having the given dimensions, this plot can be taken as being generally representative of similarly dimensioned capillary tubes 26. In any event, it will be noted that when the working pressure "$p_w$" (e.g. 450 psia) maintains the fluid refrigerant in its liquid state 50 (i.e. "refrigerant in excess") as it transits the lumen 30 of capillary tube 26, the tip temperature "$T_t$" in cryo-chamber 38 will be minimized. On the other hand, if the fluid refrigerant is allowed to boil and become gaseous (i.e. "refrigerant limited") inside the lumen 30, the tip temperature "$T_t$" rises sharply.

While the particular Improved Distal End for Cryoablation Catheters as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A heat transfer system which comprises:
   a hollow supply tube having a proximal end and a distal end;
   a capillary tube having a proximal end and a distal end with the proximal end thereof connected in fluid communication with the distal end of said supply tube, said capillary tube being formed with a lumen having a length "l" and a diameter "d";
   a tip member positioned to surround the distal end of said capillary tube to create a cryo-chamber therebetween; and
   a source of refrigerant fluid connected in fluid communication with the proximal end of the supply tube to introduce the refrigerant fluid into the supply tube wherein said fluid refrigerant has been pre-cooled to approximately −45° C. at a working pressure "$p_w$" of approximately 400 psia for transfer of the refrigerant fluid through said supply tube and through said capillary tube for exit from the distal end of said capillary tube and into said cryo-chamber in a substantially liquid state for transition of the refrigerant fluid into a gaseous state with a tip pressure "$p_t$" and a tip temperature "$T_t$" for heat transfer through said tip member and into the gaseous fluid refrigerant in said cryo-chamber;
   wherein an aspect ratio "d/l" for the capillary tube is in a range of 0.0008 to 0.0017.

2. A system as recited in claim 1 wherein said supply tube is formed with a lumen having a length "$l_s$" and a diameter "$d_s$", and wherein the diameter of the lumen of said capillary tube "d" is less than the diameter "$d_s$" and "$l_s$" is greater than or equal to the length "l".

3. A system as recited in claim 1 wherein the length "l" of said capillary tube is in a range between approximately four and one half inches and approximately ten inches.

4. A system as recited in claim 3 wherein the diameter "d" of said capillary tube is 0.008 inches.

5. A system as recited in claim 1 wherein the refrigerant fluid is nitrous oxide ($N_2O$).

6. A system as recited in claim 1 wherein the tip pressure "$p_t$" is less than one atmosphere.

7. A system as recited in claim 6 wherein the tip temperature "$T_t$" is less than minus eighty four degrees Centigrade ($T_t$<−84° C.).

8. A heat transfer system which comprises:
   a means for providing fluid refrigerant;
   a means for cooling the fluid refrigerant to approximately −45° C. at a first pressure of approximately 400 psia to transform said fluid refrigerant into a liquid state;
   a means for reducing the pressure on the liquid refrigerant from the first pressure to a second pressure; and
   a means for introducing the liquid refrigerant into a cryo-chamber at the second pressure for transition of the liquid refrigerant into a gaseous state in the cryo-chamber to cause heat to transfer from outside the cryo-chamber and into the cryo-chamber;
   wherein said reducing means comprises:
      a hollow supply tube having a proximal end and a distal end; and
      a capillary tube having a proximal end and a distal end with the proximal end thereof connected in fluid communication with the distal end of said supply tube, said capillary tube being formed with a lumen having a length "l" and a diameter "d" wherein an aspect ratio "d/l" for the capillary tube is in a range of 0.0008 to 0.0017.

9. A system as recited in claim 8 wherein the length "l" of said capillary tube is in a range between approximately four and one half inches and approximately ten inches and the diameter "d" of said capillary tube is in a range between approximately 0.008 inches and approximately 0.010 inches.

10. A system as recited in claim 8 wherein the second pressure is a tip pressure "$p_t$" less than one atmosphere.

11. A system as recited in claim 10 wherein the refrigerant in the gaseous state in the cryo-chamber has a tip temperature "$T_t$" less than minus eighty four degrees Centigrade ($T_t$<−84° C.).

12. A system as recited in claim 8 wherein the liquid refrigerant is nitrous oxide ($N_2O$).

13. A method for transferring heat which comprises the steps of:
   providing a fluid refrigerant;
   cooling said fluid refrigerant to approximately −45° C. at a first pressure of approximately 400 psia to transform said fluid refrigerant into a liquid state;
   reducing the pressure on the liquid refrigerant from the first pressure to a second pressure; and
   introducing the liquid refrigerant into a cryo-chamber at the second pressure for transition of the liquid refrigerant into a gaseous state in the cryo-chamber to cause a transfer of heat outside the cryo-chamber and into the cryo-chamber;
   wherein said reducing step comprises the steps of:
      advancing the liquid refrigerant through a hollow supply tube to a capillary tube having a proximal end and a distal end; and
      causing the liquid refrigerant to flow through the lumen of the capillary tube wherein the lumen of the capillary tube has a length "l" and a diameter "d" with an aspect ratio "d/l" for the capillary tube in a range of 0.0008 to 0.0017.

14. A method as recited in claim 13 wherein the length "l" of said capillary tube is in a range between approximately four and one half inches and approximately ten inches and the diameter "d" of said capillary tube is in a range between approximately 0.008 inches and approximately 0.010 inches.

15. A method as recited in claim 13 wherein the second pressure is a tip pressure "$p_t$" less than one atmosphere.

16. A method as recited in claim 13 wherein the liquid refrigerant is nitrous oxide ($N_2O$) and when in the gaseous state in the cryo-chamber has a tip temperature "$T_t$" less than minus eighty four degrees Centigrade ($T_t$<−84° C.).

* * * * *